United States Patent [19]

Ishii

[11] Patent Number: 4,675,661

[45] Date of Patent: Jun. 23, 1987

[54] LIGHT-ATTENUATION TYPE FIRE DETECTOR ASSEMBLY

[75] Inventor: Hiromitsu Ishii, Chiba, Japan

[73] Assignee: Hochiki Kabushiki Kaisha, Tokyo, Japan

[21] Appl. No.: 807,979

[22] Filed: Dec. 12, 1985

[30] Foreign Application Priority Data

Dec. 18, 1984 [JP] Japan .............................. 59-267230

[51] Int. Cl.⁴ .......................................... G08B 17/10
[52] U.S. Cl. ................................. 340/630; 250/573
[58] Field of Search ........................ 340/628, 629, 630; 250/573, 574, 575, 565; 356/438, 439

[56] References Cited

U.S. PATENT DOCUMENTS

| | | | |
|---|---|---|---|
| 2,763,853 | 9/1956 | Grant, Jr. ..................... | 340/630 X |
| 3,255,441 | 6/1966 | Goodwin et al. ............. | 340/630 X |
| 3,553,462 | 1/1971 | Johnson ....................... | 250/565 |
| 3,994,603 | 11/1976 | Paschedag .................... | 340/630 X |
| 4,018,534 | 4/1977 | Thorn et al. .................. | 250/575 X |
| 4,266,220 | 5/1981 | Malinowski ................... | 340/630 |
| 4,317,113 | 2/1982 | Honma ......................... | 250/565 X |
| 4,420,346 | 12/1983 | Malinowski ................... | 340/630 |
| 4,556,873 | 12/1985 | Yamada et al. ................ | 340/630 |
| 4,559,453 | 12/1985 | Muggli et al. ................. | 340/630 X |

Primary Examiner—James L. Rowland
Assistant Examiner—Daniel Myer
Attorney, Agent, or Firm—Lackenbach Siegel Marzullo & Aronson

[57] ABSTRACT

A light-attenuation type fire detector assembly of the present invention comprises a light emission drive section including a light emitter for radiating light having an intensity corresponding to an input signal level; a smoke detecting section including a light receiver which directly receives the light radiated from the light emission drive section and is adapted to output a detection signal corresponding to the received light amount of the light receiver; a smoke amount computing section for computing the amount of smoke based on the detection signal from the smoke detecting section; a delay circuit for retarding input of the detection signal from the smoke detecting section to the light emission drive section for a predetermined time; and a control section for repeating the operations of the light emission drive section, the smoke detecting section and the delay circuit and generating a control signal after a predetermined period of time has been passed or a predetermined times of operation has been done to drive the smoke amount computing section, and wherein the amount of smoke is computed during a time when said smoke amount computing section is driven based on the smoke detection signal input to said smoke amount computing section to detect if there is attenuation in the radiated light due to smoke between the light emitter and the light receiver.

18 Claims, 10 Drawing Figures

LIGHT-ATTENUATION TYPE FIRE DETECTOR ASSEMBLY

BACKGROUND OF THE INVENTION

1. Field of the Invention

This invention relates to a light-attenuation type fire detector assembly, and more particularly to a light-attenuation type fire detector assembly in which a light emitting section and a light receiving section are disposed so as to oppose each other at a given distance therebetween to form a smoke detecting space between them so that if smoke enters the smoke detecting space, the light receiving section receives light attenuated by the smoke to detect a fire, on the basis of the photo-output from the light receiving station.

2. Relevant Arts

In a conventional light-attenuation type fire detector assembly, a light emitting section for emitting light and a light receiving section for receiving the light from the light emitting section are disposed face to face so as to be spaced by a given distance from each other to form a smoke detecting space therebetween. If smoke enters the smoke detecting space, the light from the light emitting section is attenuated by the smoke and it is detected by the light receiving station. Fire detection is made based on the photo-output from the light receiving section. In such a fire detector assembly, to form an optical path of a required length, 1 m for example, within the limited space of a casing, the light emitted from the light emitting section is reflected several times by mirrors before it reaches the light receiving section. This extension of the optical path provides an effect equivalent to making the smoke detecting space larger. As a result, the attenuation by smoke is increased and the detection sensitivity is increased.

In a light-attenuation type fire detector assembly of this type, however, not only is the emitted light from the light emitting section attenuated by every reflection from the mirrors, but also the attenuation factor is increased due to blurring caused by, dirt or dust build-up etc. on the mirrors. In addition, there is the problem that the optical adjustment mechanism for the mirrors is very complicated and manufacture of the assembly is expensive.

To solve the problems described above, there has been proposed a light-attenuation type fire detector in which a plurality of light receiving sections are provided opposite to and spaced from corresponding light emitting sections, respectively, and which is operated in such a manner that the light emitted from the respective light emitting sections is received by the corresponding light receiving sections. Smoke detection signals indicative of the light attenuation at the respective light receiving sections are integrated by integrating means to determine the amount of smoke so as to obtain, at a reduced cost, an effect equivalent to enlargement of the smoke detecting space.

This type of light-attenuation type fire detector assembly, however, has the problem that it requires a plurality of light emitting sections and an equal number of light receiving sections.

The present invention contemplates a light-attenuation type fire detector assembly which does not use a plurality of light emitting sections and light receiving sections and is capable of reducing the cost and size of the entire assembly.

Prior art relevant to the present invention comprises: U.S. Pat. No. 4,018,534 issued Apr. 19, 1977 to Lawrence B. Thorn et al., U.S. Pat. No. 4,266,220 issued May 5, 1981 to William J. Malinowski et al., U.S. Pat. No. 4,420,746 issued Dec. 13, 1983 to William J. Malinowski et al., U.S. Pat. No. 3,553,462 issued Jan. 5, 1971 to Dennis F. Johnson and U.S. Pat. No. 3,994,603 issued Nov. 30, 1976 to Hansjoachim Paschedag.

SUMMARY OF THE INVENTION

The present invention is directed to obviating the problems of the prior art is described above, and provides a light-emitting type fire detector assembly which is substantially as effective as would be obtained by extending the optical path between the light emitting section and the light receiving section and enlarging the smoke detecting space within the limited space of the detector casing. It may employ only one pair of light emitting and light receiving sections, and is capable of remarkably reducing the cost and size of the fire detector assembly.

In accordance with the present invention, there is provided a light-attenuation type fire detector assembly having a light emission drive section including a light emitter adapted to emit light of an intensity corresponding to an input signal level, and a smoke detecting section including a light receiver for receiving the light from the light emission drive section, possibly attenuated by smoke, and adapted to produce a detection signal corresponding to the received light intensity. The detector assembly also includes a smoke amount computing section for computing a smoke amount based on the detection signal from the smoke detecting section. The fire detector assembly is characterized in that the detection signal from said smoke detecting section is returned to the input of the light emission drive section after a delay of a predetermined time period set by a delay circuit, and this operation is cyclically repeated during a predetermined period of time. The smoke amount computation is initiated by a control signal from a control section after such predetermined period of time, such computation being based on the smoke detection signal.

DESCRIPTION OF THE PREFERRED EMBODIMENTS

Figure 1:
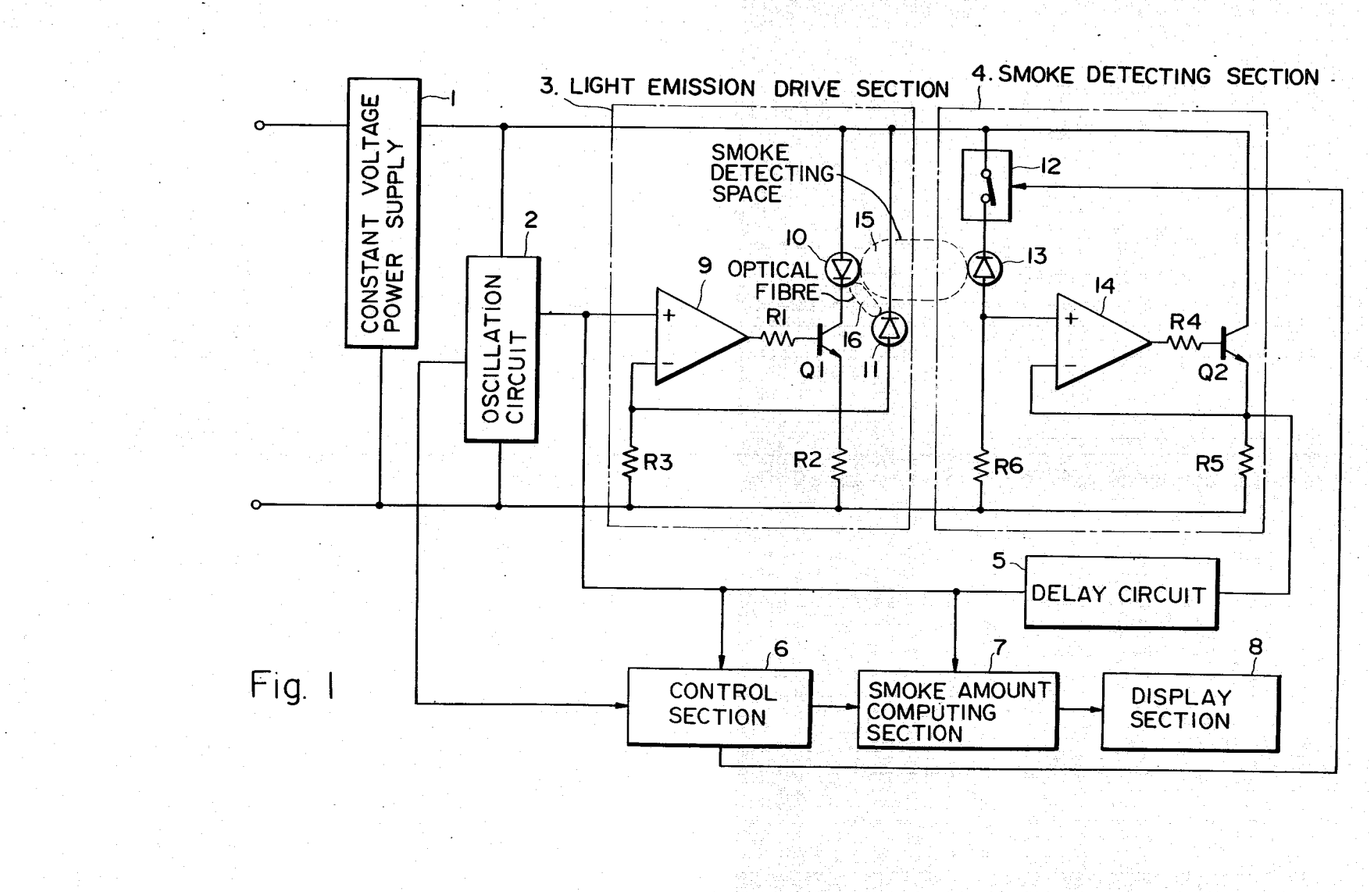
FIG. 1 is a circuit diagram of a first form of a light-attenuation type fire detector assembly according to the present invention.
Figure 2:
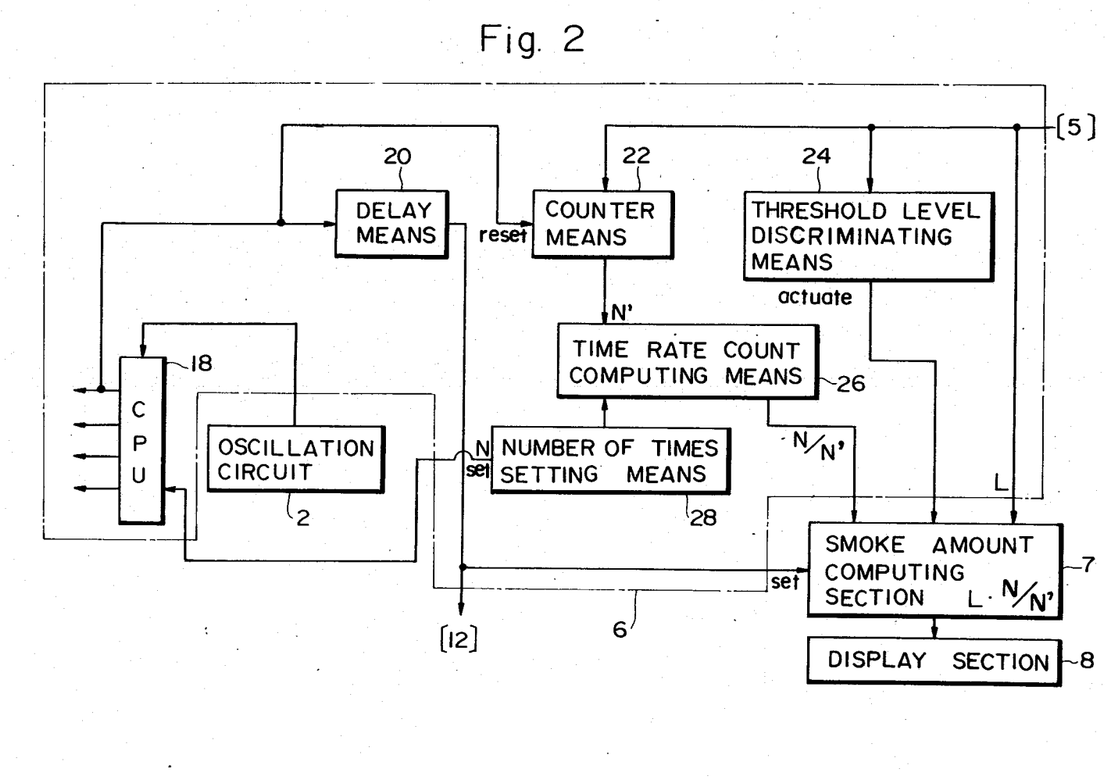
FIG. 2 is an electrical block diagram of a control section.
Figure 3:
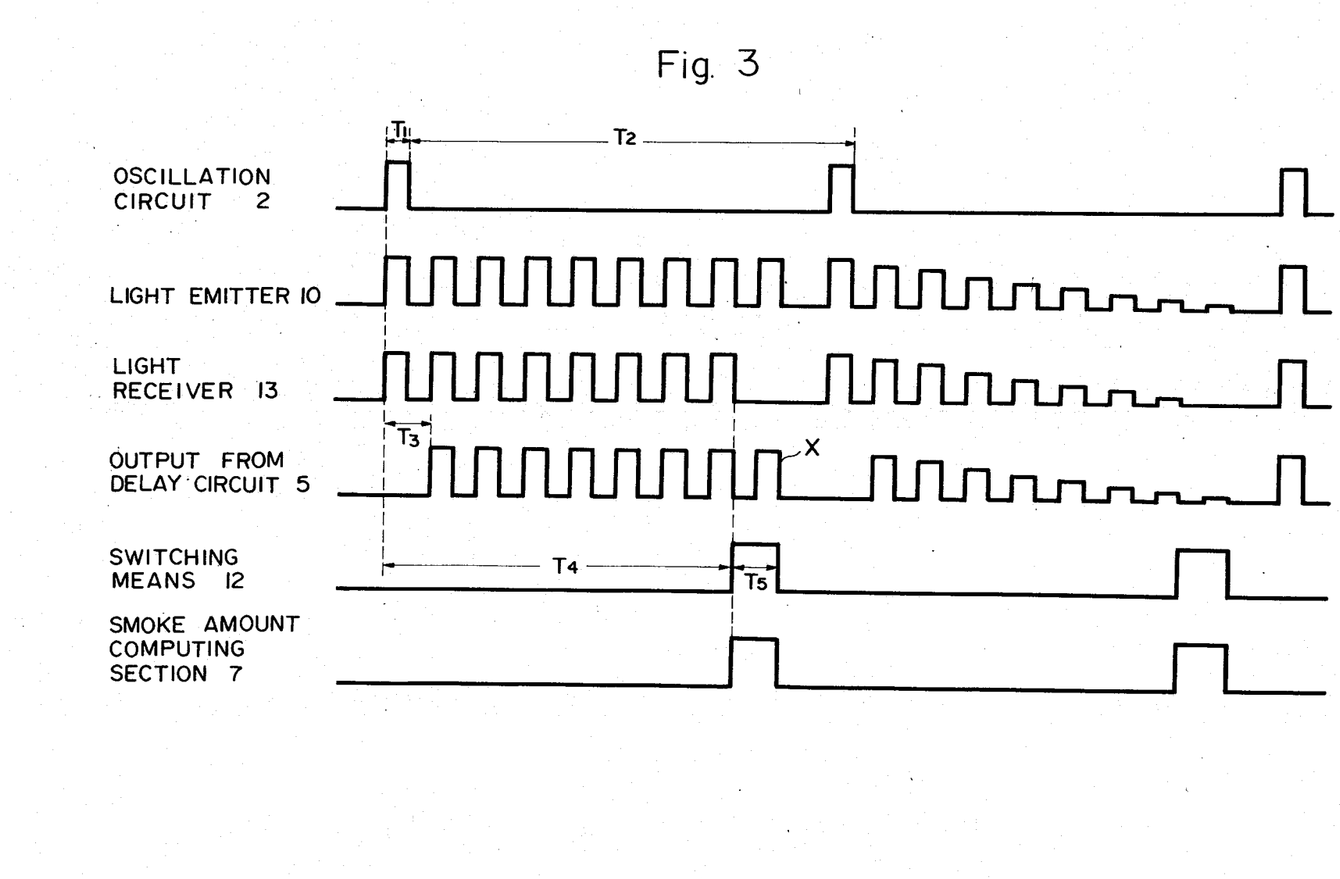
FIG. 3 is an explanatory diagram of the operation of the circuit illustrated in FIG. 1.

FIG. 1 to FIG. 3 are circuit diagrams of a first embodiment of the present invention. The formation of the circuit will first be described. A constant-voltage power source 1 outputs a constant voltage. An oscillation circuit 2 outputs a light emitting pulse having a pulse width T1 with a period of T2. A light emission drive section 3 includes a light emitter which receives, as an input, a light emitting pulse from the oscillation circuit 2 or a signal pulse from a delay circuit 5, as will be described in detail hereinafter and emits light of an intensity corresponding to the input signal level. With respect to the circuit within the light emission drive section 3, 9 is an operational amplifier and 11 is a light receiver. The operational amplifier and the light receiver 11 constitute a compensation circuit. An output terminal of the operational amplifier 9 is connected to a base of a transistor Q1 through a resistor R1. A light emitter 10, the transistor Q1 and a resistor R2 are connected in series between power lines derived from the constant-voltage power source 1. The light receiver 11 receives light emitted from the light emitter 10 through an optical fiber 16. An anode side of the light receiver 11 is connected to a resistor R3 and an inverting input terminal of the operational amplifier 9. The light receiver 11 feeds back a photo-output corresponding to the intensity of incident light emitted from the light emitter 10 to the inverting input terminal of the operational amplifier 9 to limit the intensity of light radiated from the light emitter 10 according to the input signal level, while attaining compensation for dirt build-up of the light emitter and a change in temperature. More particularly, when the intensity of the light radiated from the light emitter 10 decreases due to the dirt on the light emitter 10 or a change of an ambient temperature, the current flowing through the light receiver 11 is reduced and the voltage across the resistor R3 drops so that the output from the operational amplifier 9 is increased to prevent lowering of the intensity of the light radiated from the light emitter 10.

A smoke detecting section 4 receives light radiated from the light emission drive section 3 which is attenuated by smoke when there is intervening smoke and outputs a smoke detection signal corresponding to the received light intensity. With respect to the specific form of the circuit of the smoke detecting section 4, it includes a switching means 12 which is normally closed but is opened by a control instruction from a control section, as will be described in detail later. A light receiver 13 and a resistor R6 are connected in series between the power lines derived from the constant-voltage power source 1. The light receiver 13 is disposed so that it may directly receive the light radiated from the light emitter 10 through a smoke detecting space 15, attenuated by smoke entering the smoke detecting space 15, and supplies a photo-output to a non-inverting input terminal of an operational amplifier 14. An output terminal of the operational amplifier 14 is connected to the base of a transistor Q2 through a resistor R4. Between the power lines derived from the constant-voltage power source 1, the transistor Q2 and a resistor R5 are connected in series. The smoke detection signal at the junction point of the emitter of the transistor Q2 and the resistor R5 is fed back to an inverting input terminal of the operational amplifier 14. The detection signal voltage thus fed back is the same as that of the photo-output from the light receiver 13, and is also supplied to a delay circuit 5. The delay circuit 5 outputs such signal after a delay of a predetermined period of time T3 which is longer than the pulse width T1 but shorter than the period T2. The output of delay circuit 5 is connected to a control section which comprises a clock circuit including a delay means 20 therein as shown in FIG. 2. When a light emitting pulse from oscillation circuit 2 is input to a central processing unit (CPU) 18 is the control section 6, CPU 18 resets a counter means 22 and outputs a control signal to the smoke amount computing section 7, by the delay means 20, after a delay of a predetermined period of time T4 following the light emitting pulse. The delay time T4 is longer than the delay time T3 but shorter than the pulse period T2. The light emission drive section 3 and the smoke detecting section 4 are driven during the predetermined delay time T4. More specifically, the smoke detection signal from the smoke detecting section 4 which is obtained in response to the light emitting pulse from the oscillation circuit 2 is delayed for the period of time T3 and repeatedly input to the light emission drive section 3 to sequentially drive the smoke detecting section 4. The period of time T4 is so determined that the effective length of the smoke detecting space 15 is substantially equal to the actual length of 1 m by selecting the number of repetitions of the smoke detection signal. The control section 6 further comprises a threshold level discriminating means 24 in which a predetermined threshold level is preset. When the threshold level discriminating means 24 determines that the signal level of the signal pulse from the delay circuit 5 falls below the threshold level within the predetermined period of time T4, it transmits an actuating signal to the smoke amount computing section 7. An input of a time rate counting computing means 26 receives as an input from counter 22 a signal signifying the time (N') until the time of such actuating signal, and also receives at another input a signal signifying the predetermined period of time T4 (N) from a number of times setting means 28. From N and N', computing means 26 computes a time rate count (N/N') and outputs the time rate count as a control signal to the smoke amount computing section 7. Alternatively, the actual counts N and N' could be employed instead of the time rate count. Because of the delay circuit 5 the signal is periodically based on the ;number of oscillator pulses in the predetermined time interval which is counted by the counter means 22. The smoke amount computing section 7 is continuously input with the signal pulse from the delay circuit 5 and initiates the computation in response to the control signal from the control section 6. The smoke amount computing section 7 computes an amount of smoke according to the signal level of the signal pulse obtained within a predetermined period of time T5 preset to be twice as long as the pulse width T1 of the light emitting pulse. The smoke amount computing section 7, input with the time rate count from the control section 6, corrects the amount of smoke based on the input time rate count. More specifically, the smoke amount computing section 7 normally initiates the computation based on the control signal from the control section 6 every period of time T4. It also initiates the computation when the time rate count is input from the control section 6 due to entrance of a great amount of smoke. In the latter case, the computed amount of smoke is multiplied by the time rate count. 8 is a display section and it indicates the amount of smoke, based on the signal from the smoke amount computing section 7.

FIG. 3 is a diagram showing signal waveforms of various portions of the circuit of FIG. 1. The operation of the present embodiment will now be described referring to FIG. 3.

With respect to the operation at a normal time, as shown in FIG. 3, oscillation pulses having a pulse width T1 are output from the oscillation circuit 2 with the period T2. When the light emission drive sectin 3 is input with a first oscillation pulse for producing the basic light from the oscillation circuit 2, the operational amplifier 9 is actuated to allow the transistor Q1 to conduct. Upon conducting of the transistor Q1, the light emitter 10 radiates light. When the light radiated from the light emitter 10 is incident upon the light receiver 11 through the optical fiber 16, the light receiver 11 is turned on and the photo-output is fed back to the inverting input terminal of the operational amplifier 9. Thus, the light emitter 10 radiates light having an intensity corresponding to the signal level of the oscillation pulse input to the non-inverting input terminal of the operational amplifier 9. At a normal time, since there exists no smoke in the smoke detecting space 15, the light irradiated from the light emitter 10 enter the light receiver 13 without being attenuated. When the photo-output from the light receiver 13, which has been rendered conductive upon receipt of the light from the light emitter 10, is supplied to the non-inverting input terminal of the operational amplifier 14, the transistor Q2 is allowed to conduct to output to delay circuit 5 a detection signal having a signal level the same as the photo-output. The delay circuit 5 outputs the input detection signal to the light emission drive section 3 after a delay of the predetermined period of time T3. The light emission drive section 3 and the smoke detecting section 4 are then again driven as described. More specifically, during time period T4 the detection signal is repeatedly supplied to the light emission section 3 at intervals of the predetermined delay T3 of the delay circuit 5, so as to make the light emitter 10 radiate light of an intensity corresponding to the input signal level and drive the smoke detecting section 4. These series of operations are repeated until the predetermined period of time T4 after the outputting of the first light emitting pulse, when the switching means 12 is opened by an instruction from the control section 6 and at the same time an control signal is output to the smoke amount computing secton 7. The smoke amount computing section initiates the computing operation in response to the control signal from the control section, more particulary the signal from the time rate count computing means, and computes an amount of smoke based on the signal level of the single signal pulse (as shown X in FIG. 3) which is output from the delay circuit 5 during the predetermined period of time T5 during which the switching means remains open. More particularly, under normal conditions there is no smoke in the smoke detecting space 15. The light radiated from the light emitter 10 therefore enters the light receiver 13 without being attenuated and the signal level of the detection signal from the smoke detecting section 4 obtained through the delay circuit 5 is substantially the same as the signal level of the first oscillation pulse, so that the smoke amount computing section 7 computes the amount of smoke to be zero. The display section 8 then displays a numerical indication that the amount of smoke is zero, based on the signal from the smoke amount computing section 7.

The oscillation circuit oscillates the second pulse for producing the basic light a predetermined time T2 after the oscillation of the first pulse for producing the basic light, under the control of the CPU 18. Of course by then the time T5 in which the switching means 12 is opened has already passed and the switching means 12 is closed. The contents of the counter means 22 is cleared and reset by the second pulse. Counter means 22 then again counts the output pulses from the delay circuit 5 which are output after the predetermined time T3. That is, the circuit of the present embodiment repeats the above mentioned action during the predetermined period T2.

The operation when a fire is detected will now be described.

As shown in FIG. 3, when a second oscillation pulse is output from the oscillation circuit 2 and if smoke due to a fire enters the smoke detecting space 15, the light radiated from the light emitter 10 enters the light receiver 13 after being attenuated by the smoke. The light receiver 13 receives the light attenuated by the smoke and outputs a signal voltage corresponding to the received light amount to the non-inverting input terminal of the operational amplifier 14. The operational amplifier 14 makes the transistor Q2 conduct and outputs to the delay circuit 5 a detection signal having a signal voltage equal to the photo output of the light receiver 13. The delay circuit 5 outputs the input detection signal again to the light emission section 3 after a delay of the predetermined period of time T3. Similarly, the series of operations are repeated during the predetermined period of time T4 until the smoke amount computing section 7 is driven. More particularly, when a signal pulse attenuated by the smoke is again supplied to the light emission drive section 3, the light emitter 10 radiates light having an intensity corresponding to the signal level of the input signal pulse and the light radiated from the light emitter 10 is incident upon the light receiver 13 after being further attenuated by the smoke existing in the smoke detecting space 15. The smoke detecting section 4 therefore outputs a signal the amplitude of which corresponds to the sequentially integrated smoke attenuation When the control section 6 determines that the predetermined period of time T4 has been passed from the time when a second oscillation pulse for producing the basic light has been output from the oscillation circuit 2, the switching means 12 is opened by the control signal which is also output to the smoke amount computing section 7. The smoke amount computing section 7 initiates the computation operation in response to the control signal from the control section 6, and receives as inputs attenuated signal pulses obtained during the predetermined period of time T5 that switching means 12 is opended, and computes the amount of smoke according to the signal level of the input signal pulses. The display section 8 indicates the amount of smoke by numerals, based on the signal from the smoke amount computing section 7.

The operation when a fire spreads out will be described.

If the amount of smoke entering the smoke detecting space 15 is increased due to spread out of a fire, the attenuation of the signal level of the detection signal output from the smoke detecting section 4 is increased. The threshold level discriminating means 24 of the control section 6 which monitors the signal level of the signal pulse from the delay circuit 5 determines that the signal level has dropped below the threshold level before the predetermined period of time T4 has been passed, and a control signal as well as the time rate count (N/N') is output to the smoke amount computing section 7. The smoke amount computing section 7 receives as inputs the control signal from the control section 6 and the time rate count (N/N') and corrects the smoke amount based on the time rate count (N/N') and the present signal level L, that is, (L·N/N'). The display section 8 indicates by numerals the amount of smoke, in response to the signal from the smoke amount counting section 7.

Although the computed smoke amount is numerically indicated by the display section 8 in the above-mentioned embodiment, the analog signal representing the amount of smoke computed by the smoke amount computing section 7 may be output as it is to a fire signal receiver (not shown).

Further early smoke computing is done when the signal level falls below the thresold level in the threshold level discriminating means 24 of the control section 6. It is possible to set a higher value of the threshold level for judgement of the level corresponding to fire. If the signal level exceed the fire level the fire alarm signal is output to the display section 8 or to a fire signal receiver (not shown). Quick response to a sudden decrease of the signal level can be achieved.

A second embodiment of the present invention will now be described referring to FIGS. 4 and 5.

Figure 4:
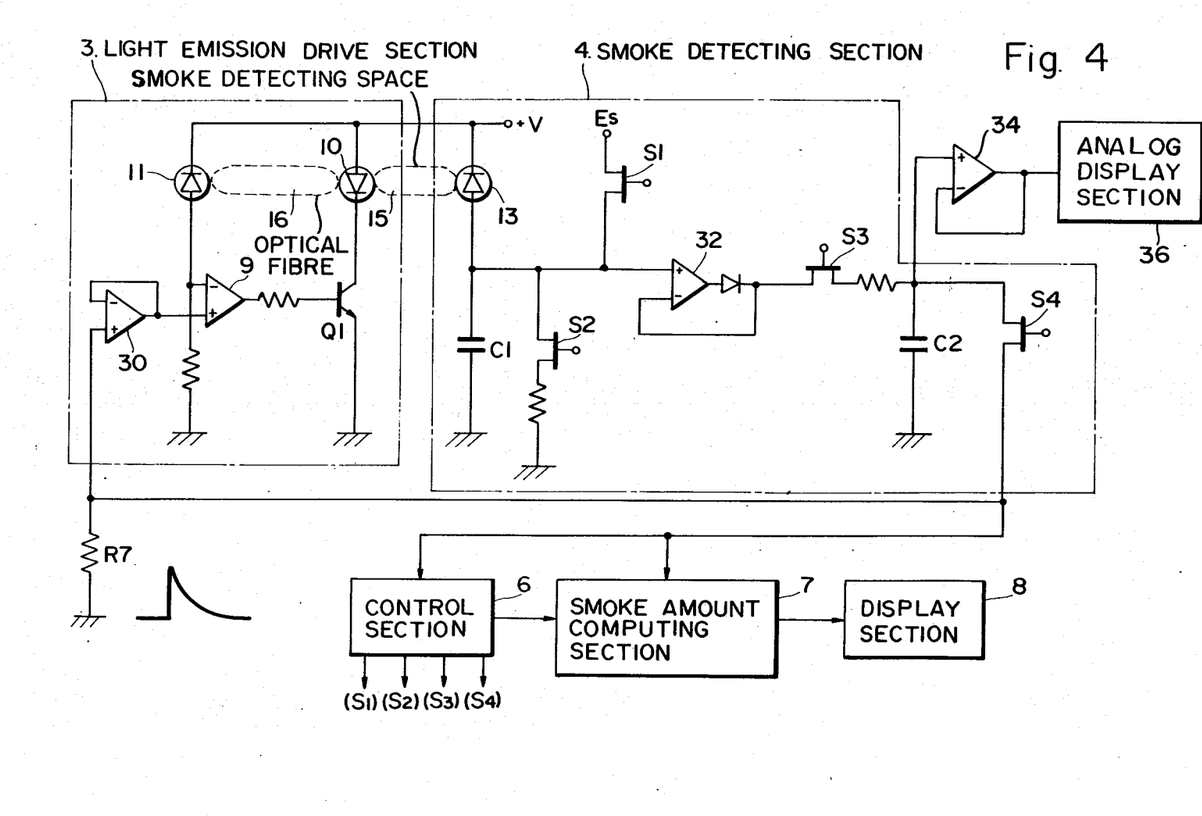
FIG. 4 is a circuit diagram of a second form of a light-attenuation type fire detector assembly according to the present invention.
Figure 5:
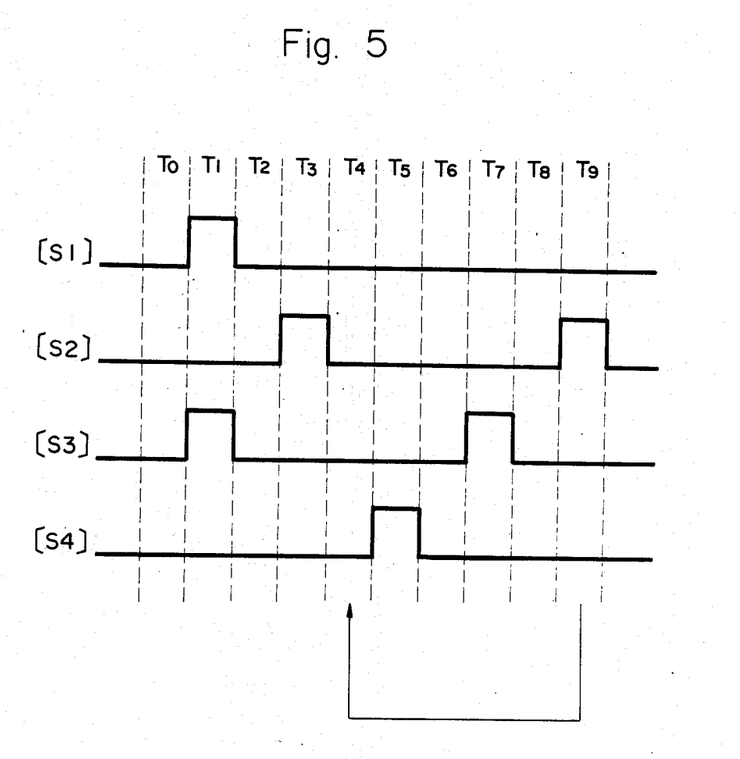
FIG. 5 is an explanatory diagram of the operation of the same.

FIG. 4 is a circuit diagram of a second form of light-attenuation type fire detector assembly according to the present invention and FIG. 5 is a timing chart of the same.

In the first embodiment of the present invention as described above, since the delay circuit 5 is comprised of a delay element or the like, there may be caused a transmission distortion which possibly prevents detection of an accurate value. For this reason, a delay is attained by charge transfer between capacitors using the switching means in the second embodiment to prevent transmission distortion from being caused.

More specifically, as illustrated in FIG. 4, a first capacitor C1 is connected to an end of the light receiver 13 and to a switch S1 for supplying a predetermined reference voltage and a switch S2 for completely removing the residual charge in the capacitor. The capacitor C1 is further connected to a switch S3 as a first switching means through a buffer 32 so that when the switch S3 is closed, the voltage defined by the charge stored in the capacitor C1 is applied to the second capacitor C2 and a charge corresponding to the voltage is charged in the capacitor C2. The capacitor C2 is connected to a switch S4 as a second switching means and when said switch S4 is closed, the charge stored in the capacitor C2 is output to a buffer 30. The output to the buffer 30 becomes a differentiated waveform, as shown, which is determined by the capacitor C2 and a resistor R7. The buffer 30 is connected to the non-inverting input terminal of the operational amplifier 9 so that when the switch S4 is closed, an output signal is generated by the operational amplifier 9 to allow the transistor Q1 to conduct and the light emitter 10 to radiate light. The light receiver 13 receives the light and a charge corresponding to the received light amount is stored in the capacitor C1. The switches S1, S2, S3 and S4 are connected to the control section 6 and are controlled by it. The capacitor C2 is further connected to an analog display section 36 through a buffer 34 and an analog indication is made according to the amount of charge stored in the capacitor C2. However, direct reading of the charge stored in the capacitor C2 at the time of the completion of the predetermined times of the light emmission can be attained by connecting the output of the buffer 34 to a fire signal receiver which is not shown. In that case, the receiver will detect if there is any attenuation of the light due to smoke without any reference to the smoke amount computing section 7. That would be hightly suitable for smoke detection under normal conditions.

The entire operation of this embodiment will be described referring to FIG. 5.

During T1, the switch S1 and the switch S3 are closed and predetermined reference voltages are charged in the capacitor C2 and the capacitor C1. During succeeding time interval T3, the switch S2 is closed and an excess voltage stored in the capacitor C1 is discharged. During T5, the switch S4 is closed and the charge stored in the capacitor C2 is output to the light emission drive section 3 so that the light emitter 10 radiates light and the light receiver 13 receives the light. As a result, a voltage corresponding to the received light amount is stored in the capacitor C1. During T7, the switch S3 is again closed and the charge correspond to the charge stored in the capacitor C1 is stored in the capacitor C2. In other words, a period of time T6 becomes a delay time. During succeeding period T9, the switch S2 is closed to completely remove the residual charge in the capacitor C1 in preparation for storing a voltage accurately corresponding to the received light amount. These operations (from T4 to T9) are repeated several times and thereafter operations similar to those of the first embodiment are made to provide indication on the display section 8. At the next time interval T1, the charge for producing the basic light is charged in the capacitor C1 and C2, and the same operation will be repeated.

According to this embodiment, since the delay circuit is formed without using a delay element or the like, generation of transmission distortion can be prevented and accurate fire information can be attained.

A third embodiment of the present invention will now be described referring to FIGS. 6 and 7.

In the third embodiment, a delay circuit is constituted by the switches S1, S2, S3 and S4 and the capacitors C1 and C2 as in the second embodiment, but a second switching means is constituted by a square wave generating circuit 39 which is different from the second embodiment.

Figure 6:
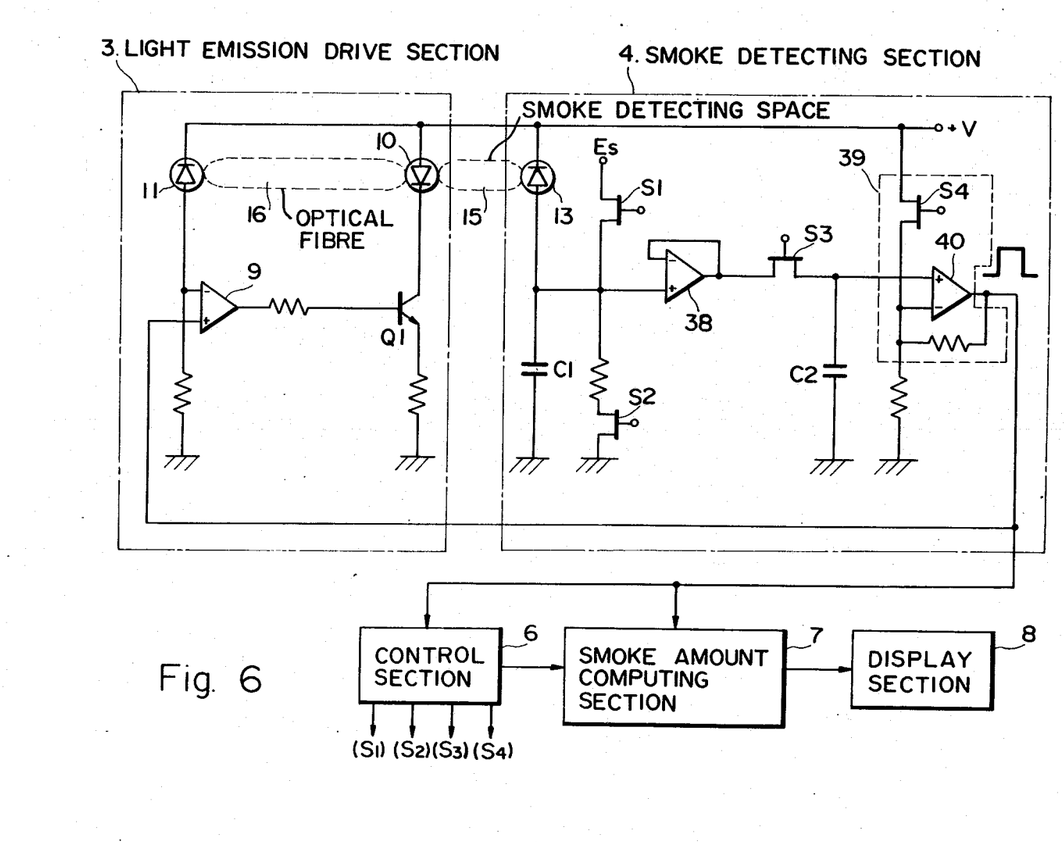
FIG. 6 is a third form of a light-attenuation type fire detector assembly according to the invention.
Figure 7:
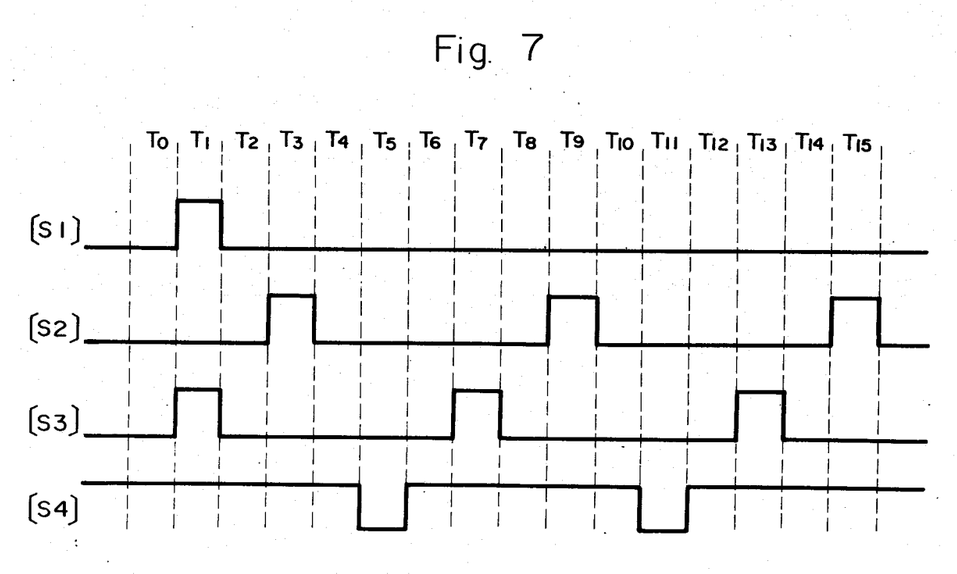
FIG. 7 is an explanatory diagram of the operation of the same.

The square wave generating circuit 39 is composed of the switch S4 and an operational amplifier 40 as illustrated in FIG. 6. The operational amplifier 40 is provided with a negative feedback and the switch S4 is connected to an inverting input terminal of the operational amplifier 40. The non-inverting input terminal of the operational amplifier 9 is connected to an output terminal of the capacitor C2. The remaining portion of FIG. 6 is identical with that of the foregoing first and second embodiments.

The entire operation of the embodiment in FIG. 6 will be described referring to FIG. 7.

During T1, the switches S1 and S3 are closed and predetermined reference voltages are charged in the capacitors C2 and C1. Further the switch S4 is normally closed. During succeeding time period T3, the switch S2 is closed and an excessive voltage stored in the capacitor C1 is discharged. During T5, the switch S4 is opened and the voltage at the inverting input terminal of the operational amplifier 40 is lowered so that an output of square waveform is supplied to the light emission drive section 3 to allow the light emitter 10 to radiate light. The light receiver 13 receives the light and a voltage corresponding to the received light amount is charged in the capacitor C1. During T7, the switch S3 is again closed and the charge corresponding to the charge stored in th capacitor C1 is stored in the capacitor C2. Thus, the period of time T6 becomes a delay time. During succeeding time period T9, the switch S2 is closed and the residual charge in the capacitor C1 is completely removed in preparation for storing accurate voltage corresponding to the received light amount. The light emission of the light emitter 10 following the close action of the switch S2 and the close action of the switch S3, and also following the open action of switch S4, comprises the one action for light emittion and detection (i.e. T3 to T9,T9 to T15 each shows the one action). After the predetermined number of times of the repeat action, the switches S1 and S3 are again closed at the same time, thus completing one cycle of operation. After the completion of the cycle, the signal is output from the time rate count computing means 26 to the smoke amount computing section 7, and the display section indicates the smoke amount in accordance with the signal from the smoke amount computing section 7.

According to the embodiment in FIG. 6, since the waveform output to the light emission drive section 3 is a square wave, no influence is exerted on the integration of pulses even if the response characteristic of the entire circuit is rather poor. The light emission amount therefore becomes stable.

A fourth embodiment of the present invention will be described referring to FIGS. 8 to 10.

Figure 8:
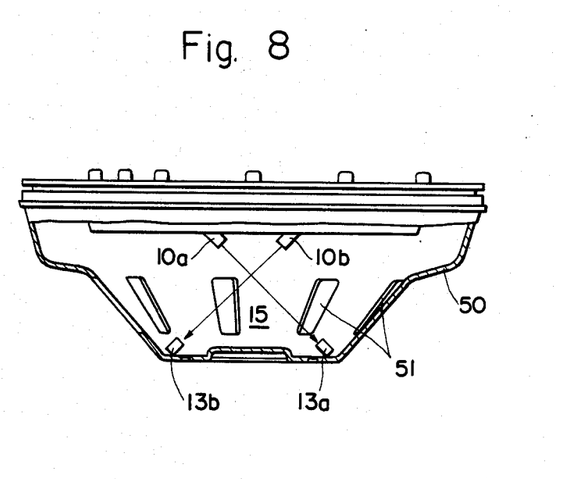
FIG. 8 is a schematic sectional view of a fourth form of a light-attenuation type fire detector assembly according to the present invention.

Although a single light emitter and a single light receiver are employed for smoke detection in the foregoing embodiments, two pairs of oppositely disposed light emitter 10a and light receiver 13a and light emitter 10b and light receiver 13b may be so arranged, for example, that the optical axes of the light emitters 10a and 10b intersect each other substantially at right angles as illustrated in FIG. 8. More specifically, 50 is a casing of the fire detector assembly which is formed in a bowl-like shape as illustrated and provided with a plurality of smoke inlets 51. The inside of the casing forms the smoke detecting space 15. The arrangement of the light emitters 10a and 10b and the light receivers 13a and 13b is not limited to the example as illustrated.

Figure 9:
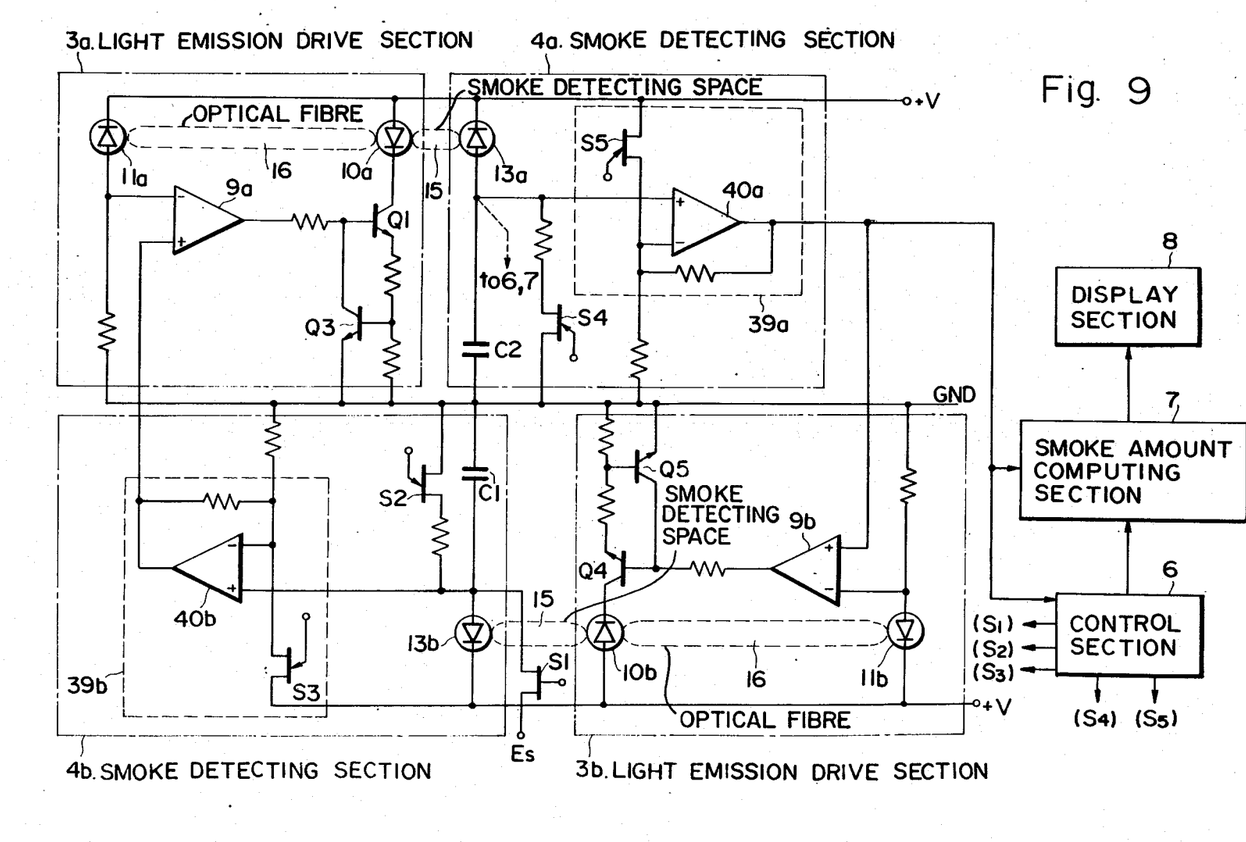
FIG. 9 is a circuit diagram of the same.
Figure 10:
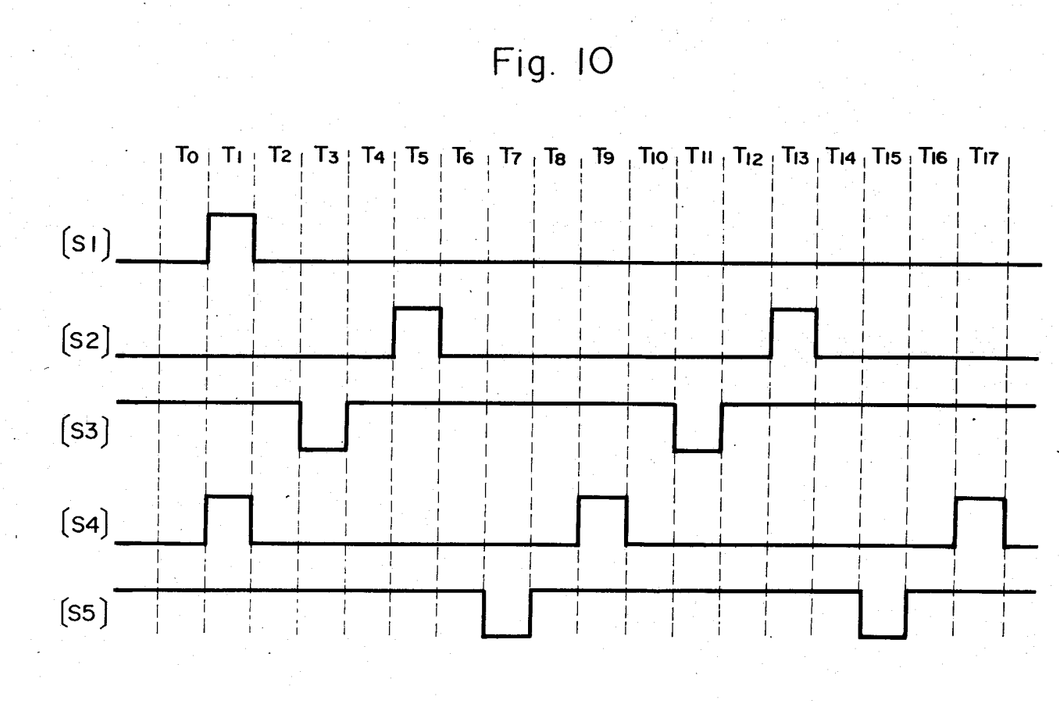
FIG. 10 is an explanatory diagram of the operation of the same.

The circuit arrangement of this embodiment is as illustrated in FIG. 9. One of the light emission drive sections 3a has a transistor Q3, so that when the transistor Q1 is rendered conductive and the light emitter 10a radiates light, the transistor Q3 is allowed to conduct at once for making the light emitter 10a radiate light instantaneously. Thus, power consumption is reduced and the operation is ensured. The light emitted from the light emitter 10a is received by the light receiver 13a and a charge corresponding to the received light amount is stored in a capacitor C2. The capacitor C2 is connected to a square wave generating circuit 39a functioning as a switching means. The square wave generating circuit 39a is composed of an operational amplifier 40a and a switch S5 as in the third embodiment as described above. The light emission drive section 3b is identical in construction with the light emission drive section 3a. The smoke detecting section 4b is substantially the same as the smoke detecting section 4a and it is constituted by a capacitor C1 and a square wave generating circuit 39b. Further the delay circuit of the embodiment in FIG. 9 is not a separate circuit as in the second embodiment. The delay function which is the main function of the delay circuit is achieved by the on-off action of the switches S3 and S5 which control the outputs of the square wave generating circuits 39a and 39b.

The entire operation of this embodiment will be described referring to FIG. 10.

During T1, the switch S1 and switch S4 are closed and the predetermined reference voltage is charge in the capacitor C1 and remaining charge in the capacitor C2 is discharged. Further the switches S3 and 5 are normally closed. During succeeding T3, the switch S3 is opened and the voltage at the inverting input terminal of the operational amplifier 40b is lowered so that a signal voltage of a square waveform is output to the light emission drive section 3a to drive the light emitter 10a. The light receiver 13a receives the light from the light emitter 10a and a voltage corresponding to the received light amount is charged in the capacitor C2. During T5, the switch S2 is closed and the residual charge in the capacitor C1 is removed. During T7, the switch S5 is opened and the voltage at the inverting input terminal of the operational amplifier 40a is lowered so that a signal voltage of a square waveform is output to the light emission drive section 3b to drive the light emitter 10b. The light receiver 13b receives the light emitted from the light emitter 10b and a voltage corresponding to the received light amount is charged in the capacitor C1. In T9, the switch S4 is closed and the remaining charge in the capacitor C2 is discharged. The light emission of the light emitter 10a following the open action of the switch S3 and the light emission of the light emitter 10b following the open action of the switch S5 comprises the one action for light emission and detection (i.e. T3 to T9,T11 to T17 each shows the one action). After the predetermined number of times of the repeat action, the switches S1 and S4 are again closed at the same time, thus completing one cycle of operation. After the completion of the cycle, the signal is output from the time rate count computing means 26 to the smoke amount computing section 7, and the display section indicates the smoke amount in accordance with the signal from the smoke amount computing section 7. The control of these switches S1, S2, S3, S4 and S5 is made by the control section 6. More particularly, in the embodiment of FIG. 9, the signal pulse is repeatedly transferred between the light emission drive section 3a, the smoke detecting section 4a, the light emission drive section 3b, and the smoke detecting section 4b to provide a delay time for smoke detection.

According to this embodiment, since two light emitters 10a and 10b and two light receivers 13a and 13b are used for smoke detection, accurate smoke detection can be attained even if the flow of the smoke is changed. Although two sets of light emitter and light receiver are employed in the fourth embodiment, more than two sets of light emitter and light receiver may be employed.

In all of the embodiments of the invention as described above, the smoke detection signal is supplied to the control section 6 and to the smoke amount computing section 7. However the object of the delay of the smoke detecting signal is feedback of the change of the light value received by the light receiver 13,13a, and 13b in accordance with smoke. That is, it would be possible to input the smoke detecting signal directly to the control section 6 and to the smoke amount computing section 7.

For example, in the first embodiment, the delay circuit 5 could be connected between the output of oscillation circuit 2 and the detection signal input to control section 6. In the second and third embodiments the control section 6 and the smoke amount computing secton 7 could be connected directly to the point where the light receiver 13 and the capacitor C1 are connected. And further, in the fourth, the control section 6 and the smoke amount section 7 could be connected directly to the point where the light receiver 13a and the capacitor C2 are connected.

Quick determination of fire can be achieved because the smoke detecting signal is input to the smoke amount computing section 7 without any delay.

I claim:

1. A light-attenuation type fire detector assembly which comprises a light emission drive section including a light emitter for radiating light having an intensity corresponding to an input signal level; a smoke detecting section including a light receiver which directly receives the light radiated from the light emission drive drive section and outpus a detection signal corresponding to the intensity of the light received by the light receiver; a smoke amount computing section for computing the amount of smoke based on the detection signal from the smoke detecting section; a delay circuit for retarding input of the detection signal from the smoke detecting section to the light emission drive section for a predetermined time; and a control section for causing repeated operation of the light emission drive section, the smoke detecting section and the delay circuit, and generating a control signal after a predetermined period of time during which a predetermined number of such operations have been repeated; the amount of smoke computed by said smoke amount computing section being based on the smoke detection signal input to said smoke amount computing section, such signal signifying the attenuation in the light received by the light receiver due to smoke between the light emitter and the light receiver.

2. A light-attenuation type fire detector assembly according to claim 1, wherein said control section includes a threshold level discriminating means which outputs a fire alarm signal when the detecting signal from the fire detecting section exceeds a predetermined threshold level corresponding to occurrence of fire in the smoke detecting section.

3. A light-attenuation type fire detector assembly according to claim 1, wherein said control section includes a threshold level discriminating means which transmits a drive signal to said smoke amount computing section when there occurs, in the detection signal from the smoke detecting section, a change exceeding a predetermined threshold level within said predetermined period of time.

4. A light-attenuation type fire detector assembly according to claim 1, wherein said delay circuit comprises a capacitor which is charged according to the received light amount and a switching means for discharging the charge stored in the capacitor.

5. A light-attenuation type fire detector assembly according to claim 1, wherein said delay ciruit comprises a first capacitor which is charged according to the received light amount; a first switching means for discharging the charge stores in said first capacitor after said predetermined period of time has passed; a second capacitor which is charged by the charge discharged from said first capacitor; and a second switching means which discharges the charge stored in said second capacitor by switching and actuates the light emitter to radiate light.

6. A light-attenuation type fire detector assembly according to claim 5, wherein said second switching means comprises a square wave generating circuit.

7. A light-attenuation type fire detector assembly according to claim 5, comprising at least two pairs of light emitters and light receivers.

8. A light-attenuation type fire detector assembly according to claim 1, which further comprises an analog display section for displaying an analog indication of the amount of smoke in response to the detection signal from said smoke detecting section.

9. A light-attenuation type fire detector assembly according to claim 1, which further comprises another light receiver for receiving the light radiated from the light emitter through a smoke-free path and a compensation circuit in the light emission drive section for compensating for dirt on the light emitter and for temperature changes by using the intensity of the light received by said second light receiver as a reference value.

10. A light-attenuation type fire detector assembly according to claim 1, comprising at least two pairs of light emitters and light receivers.

11. A light-attenuation type fire detector assembly which comprises a light emission drive section including a light emitter for radiating light having an intensity corresponding to an input signal level; a smoke detecting section including a light receiver which directly receives the light radiated from the light emission drive section and outputs a detection signal corresponding to the intensity of the light received by the light receiver; a delay circuit for retarding input of the detection signal from the smoke detecting section to the light emission drive section for a predetermined time; and a control section for causing a predetermined number of repeated operations of the light emission drive section, the smoke detecting section and the delay circuit; the detection of the attenuation in the radiated light due to smoke between the light emitter and the light receiver being based on the detection signal produced by the light receiver after said predetermined number of operations of the light emission drive section, the smoke detecting section and the delay circuit have been completed.

12. A light-attenuation type fire detector assembly according to claim 11, wherein said delay circuit comprises a capacitor which is charged according to the received light amount and a switching means for discharging the charge stored in the capacitor.

13. A light-attenuation type fire detector assembly according to claim 11, wherein said delay circuit comprises a first capacitor which is charged according to the received light amount; a first switching means for discharging the charge stored in said first capacitor after said predetermined period of time has passed; a second capacitor which is charged by the charge discharged from said first capacitor; and a second switching means which discharges the charge stored in said second capacitor by switching and actuates the light emitter to radiate light.

14. A light-attenuation type fire detector assembly according to claim 13, wherein said second switching means comprises a square wave generating circuit.

15. A light-attenuation type fire detector assembly according to claim 13, comprising at least two pairs of light emitters and light receivers.

16. A light-attenuation type fire detector assembly according to claim 11, which further comprises an analog display section for displaying an analog indication of the amount of smoke in response to the detection signal from said smoke detecting section.

17. A light-attenuation type fire detector assembly according to claim 11, which further comprises another light receiver for receiving the light radiated from the light emitter through a smoke-free path and a compensation circuit in the light emission drive section for compensating for dirt on the light emitter and for temperature changes by using the intensity of the light received by said second light receiver as a reference value.

18. A light-attenuation type fire detector assembly according to claim 11, comprising at least two pairs of light emitters and light receivers.

* * * * *